(12) United States Patent
Jang et al.

(10) Patent No.: US 8,562,815 B2
(45) Date of Patent: Oct. 22, 2013

(54) GLUCOSE SENSOR HAVING TITANIUM DIOXIDE-GRAPHENE COMPOSITE

(75) Inventors: Hee-Dong Jang, Daejeon (KR); Han-Kwon Chang, Daejeon (KR); Sun-Kyung Kim, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 0 days.

(21) Appl. No.: 13/283,018

(22) Filed: Oct. 27, 2011

(65) Prior Publication Data

US 2013/0062201 A1   Mar. 14, 2013

(30) Foreign Application Priority Data

Sep. 8, 2011 (KR) .................. 10-2011-0091512

(51) Int. Cl.
*G01N 27/327* (2006.01)

(52) U.S. Cl.
USPC ..... 205/792; 264/12; 204/403.12; 435/287.1; 422/68.1; 422/82.01

(58) Field of Classification Search
USPC ............ 204/403.01–403.15; 205/777.5, 778, 205/792; 600/345–348; 264/12; 435/287.1; 422/68.1, 82.01
See application file for complete search history.

(56) References Cited

FOREIGN PATENT DOCUMENTS

| KR | 10-2000-0008880 A | 2/2000 |
| KR | 10-2005-0019139 A | 2/2005 |
| KR | 10-2010-0131495 | 12/2010 |

OTHER PUBLICATIONS

Bao et al., New Nanostructured TiO2 for direct electrochemistry and Gluose Sensor Applications, Adv. Funct. Mater, 2008, 591-599.*
Lambert et al., Synthesis and Characterization of Titania-Graphene Nanocomposites, J.Phys. Chem.C. 2009, 113, 19812-19823.*
Kim et al.; entitled "Synthesis of TiO2-Graphene Composite by Aerosol Process," paper submitted to Nano Korea 2011, The 9th International Nanotech Symposium & Exhibition in Korea that occurred on Aug. 24-26, 2011.
Kim et al.; entitled "Preparation and Characterization of TIO2-Graphene Composite," paper submitted to the Korean Conference on Aerosol and Particle Technology that occurred Jun. 30-Jul. 2, 2011.
Fan et al. "TiO2-graphene nanocomposite for electrochemical sensing of adenine and guanine" Electrochimica Acta, Mar. 4, 2011, pp. 4685-4690, vol. 56.

* cited by examiner

*Primary Examiner* — J. Christopher Ball
*Assistant Examiner* — Jennifer Dieterle
(74) *Attorney, Agent, or Firm* — The Webb Law Firm

(57) ABSTRACT

Provided is a glucose sensor including a titanium dioxide-graphene composite having a porous structure. More particularly, the glucose sensor includes a working electrode having the titanium dioxide-graphene composite having the porous structure and an enzyme to provide features that allow a current flow to be excellent, a current to be sensitively changed depending on a change in electric potential, sensitivity to be high, and a low voltage characteristic to be excellent.

5 Claims, 7 Drawing Sheets

GLUCOSE SENSOR HAVING TITANIUM DIOXIDE-GRAPHENE COMPOSITE

CROSS-REFERENCE TO RELATED APPLICATIONS

This application claims priority under 35 U.S.C. §119 to Korean Patent Application No. 10-2011-0091512, filed on Sep. 8, 2011 in the Korean Intellectual Property Office, the disclosure of which is incorporated herein by reference in its entirety.

TECHNICAL FIELD

The following disclosure relates to a glucose sensor, and in particular, to a glucose sensor having a high output current density, very smooth movement of an electric charge, a high specific surface area, and excellent sensitivity.

BACKGROUND

Glucose as a widespread source of nutrients of an organism performs a basic role in supplying energy, storing carbon, biosynthesis, and forming carbon frames and cell walls, and glucose sensors using current measurement have been actively studied.

Most recent studies of the glucose sensor have been made based on immobilization of an enzyme such as glucose oxidase promoting oxidation of glucose to gluconolactone disclosed in Korean Patent Laid-Open Publication No. 2000-0008880, or glucose dehydrogenase disclosed in Korean Patent Laid-Open Publication Nos. 2010-0131495 and 2005-0019139.

A charge carrier needs to be typically used in an enzyme-based sensor to increase sensitivity and selectivity of the sensor.

However, a current measurement enzyme electrode has relatively low output current and sensitivity and a delayed reaction time.

Particularly, when glucose is measured as a blood sugar material in the blood of a diabetic patient, it is required that ion attraction between various interferential materials in blood is prevented using application of ultra-low voltage (0.055 V or less) and a rapid oxidase reaction is induced. Therefore, there is an earnest demand for developing a glucose sensor having a high current density and excellent sensitivity when low voltage is applied.

RELATED ART DOCUMENT

Patent Document (Patent Document 1) KR2000-0008880 A
(Patent Document 2) KR2010-0131495 A
(Patent Document 3) KR2005-0019139 A

SUMMARY

An embodiment of the present invention is directed to providing a glucose sensor having a high output current density, very smooth movement of an electric charge, a high specific surface area, and excellent sensitivity.

In one general aspect, a glucose sensor includes a titanium dioxide-graphene composite having a porous structure, and in particular, the glucose sensor includes the titanium dioxide-graphene composite having the porous structure as a charge carrier.

In particular, the glucose sensor may include an electrode to which a glucose oxidase or a glucose dehydrogenase and the composite are fixed.

In particular, a dispersion solution including graphene oxide and titanium dioxide may be sprayed dropwise, sprayed liquid droplets may be dried to obtain precursor powder of graphene oxide-titanium dioxide, and the precursor powder may be heat treated to manufacture the composite.

The dispersion solution may include 5 to 200 parts by weight of the graphene oxide based on 100 parts by weight of the titanium dioxide, and in particular, the dispersion solution may include 5 to 10 parts by weight of the graphene oxide based on 100 parts by weight of the titanium dioxide.

Preferably, the dispersion solution may be sprayed using an ultrasonic wave and the sprayed liquid droplets may be conveyed to a dry furnace using an inert gas for drying to manufacture the precursor powder, and the precursor powder manufactured by drying the sprayed liquid droplets may be heat treated in an inert gas atmosphere at 700 to 900° C. to manufacture the composite.

The composite provided in the glucose sensor may have a specific surface area of 55 to 200 $m^2/g$.

Other features and aspects will be apparent from the following detailed description, the drawings, and the claims.

DETAILED DESCRIPTION OF EMBODIMENTS

Figure 1:
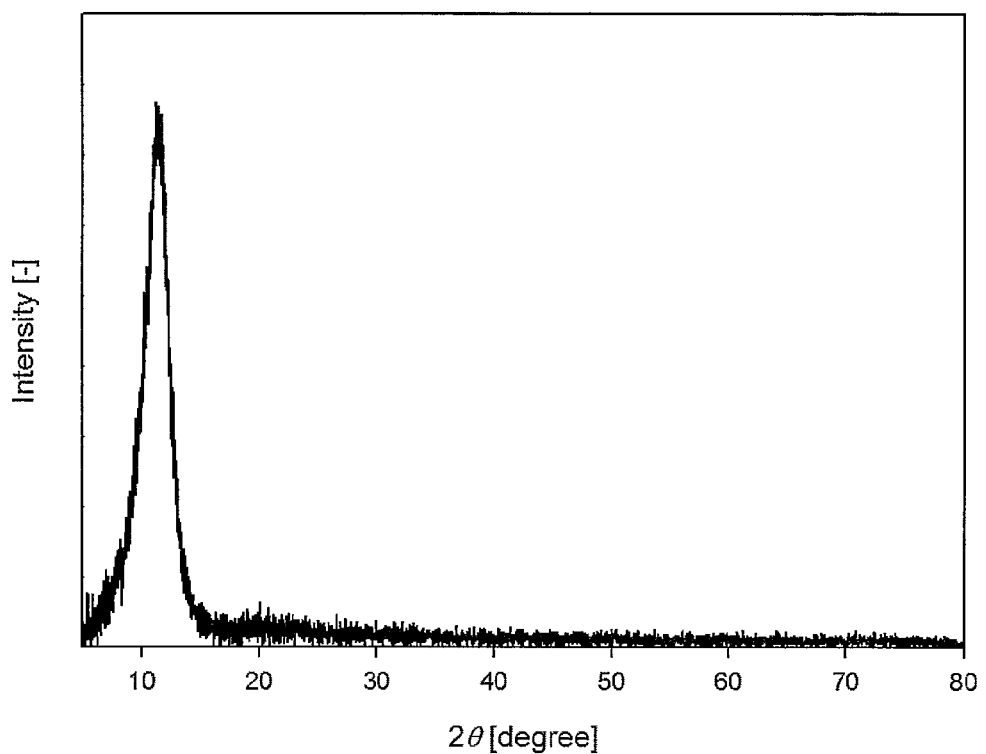
FIG. 1 shows a result of an x-ray diffraction analysis of graphene oxide manufactured using oxidation of graphite.

Hereinafter, a glucose sensor according to the present invention will be described in detail with reference to the accompanying drawings. The following drawings are provided as examples so that this disclosure will fully convey the scope of the present invention to those skilled in the art. The present invention may, accordingly, be embodied in different forms and should not be construed as limited to the drawings set forth herein, and the following drawings may be exaggerated for clarity. Further, like reference numerals designate like elements throughout the specification.

Unless it is not mentioned, all terms including technical terms and scientific terms used herein have the same meaning as the meaning generally understood by the person with ordinary skill in the art to which the present invention belongs, and a known function and configuration that unnecessarily obscures the technical gist of the present invention is omitted in the following description and the accompanying drawings.

A glucose sensor according to the present invention includes a titanium dioxide-graphene composite having a porous structure.

The glucose sensor according to the present invention may have a typical glucose sensor structure of a two electrode structure including a working electrode, a reference electrode, and an electrolyte (including an electrolyte including a material to be measured) that is provided between the working electrode and the reference electrode to provide a current moving path between the working electrode and the reference electrode.

The working electrode applies a predetermined voltage to the material to be measured in order to measure a reaction current of glucose and the enzyme, and the reference electrode provides a reference potential to measure the reaction current of glucose and the enzyme.

The glucose sensor according to the present invention may have a typical glucose sensor structure of a three electrode structure including a working electrode, a reference electrode, and a counter electrode. In the three electrode structure, a current flows between the working electrode and the counter electrode, and a potential of the working electrode is measured based on the reference electrode.

The glucose sensor according to the present invention has the two-electrode structure or the three-electrode structure, and a titanium dioxide-graphene composite having a porous structure is provided to the electrode, more particularly, the working electrode to increase a specific surface area of the working electrode and allow a current to smoothly flow.

In detail, the working electrode provided in the glucose sensor according to the present invention includes the titanium dioxide-graphene composite and the enzyme including glucose oxidase or glucose dehydrogenase, and more particularly, the working electrode includes a mixture of the titanium dioxide-graphene composite and the enzyme applied on a conductive plate. For example, the conductive plate of the working electrode includes a conductive graphite plate, the working electrode includes the conductive graphite plate and a coating layer of the mixture of the oxide-graphene composite and the enzyme applied on at least one side of the conductive graphite plate, the reference electrode includes Ag/AgCl electrodes, and the counter electrode includes a Pt electrode.

In this connection, it is preferable that the coating layer provided on the working electrode includes 100 to 300 units of enzyme based on 1 g of the titanium dioxide-graphene composite.

The titanium dioxide-graphene composite provided on the glucose sensor according to the present invention is described in detail below.

The dispersion solution including graphene oxide and titanium dioxide is sprayed dropwise, the sprayed liquid droplets are dried to obtain precursor powder of graphene oxide-titanium dioxide, and the precursor powder is heat treated to manufacture the titanium dioxide-graphene composite.

The precursor powder manufactured using spraying and drying of the liquid droplets is heat treated to manufacture the titanium dioxide-graphene composite, and the composite is a secondary particle having a porous structure including titanium dioxide particles and graphene particles agglomerating together. The primary particles of titanium dioxide agglomerate to form a porous structure and the whole surface or a portion of the surface of porous agglomerate of titanium dioxide is covered with graphene to form a secondary particle structure, depending on a weight ratio of titanium dioxide and graphene oxide included in the dispersion solution, spraying and drying conditions of the liquid drops, and a heat treatment condition of the precursor powder.

In detail, the dispersion solution includes 5 to 200 parts by weight of the graphene oxide based on 100 parts by weight of the titanium dioxide, and more particularly, the dispersion solution includes 5 to 10 parts by weight of the graphene oxide based on 100 parts by weight of the titanium dioxide.

The covering of the surface of the porous agglomerate of titanium dioxide with graphene depends on the weight ratio of graphene oxide based on titanium dioxide included in the dispersion solution.

When the dispersion solution includes 5 to 10 parts by weight of graphene oxide based on 100 parts by weight of titanium dioxide, the composite may have a structure including the porous agglomerate of titanium dioxide partially covered with graphene on a surface thereof, and when the dispersion solution includes graphene oxide in an amount that deviates from the above range, the composite may have a structure including the porous agglomerate of titanium dioxide totally covered with graphene on the surface thereof.

Graphene oxide and titanium dioxide are used as raw materials, the dispersion solution is sprayed and preferably sprayed using an ultrasonic wave and dried, and the heat treatment is performed to reduce graphene oxide to manufacture the titanium dioxide-graphene composite having a very high specific surface area and including the secondary particles having the porous structure.

When titanium dioxide and graphene oxide are used as raw materials, sprayed using the ultrasonic wave and dried to manufacture the precursor powder, and heat treated in an inert gas atmosphere, crystallinity of titanium dioxide is maintained, only graphene oxide is reduced into graphene, and the primary particles of titanium dioxide are prevented from being sintered to form the porous agglomerate of titanium dioxide, thereby manufacturing the titanium dioxide-graphene composite having the structure including the porous agglomerate partially or totally covered with graphene on the surface thereof.

Any material may be used as a medium of the dispersion solution as long as titanium dioxide ($TiO_2$) and graphene oxide (GO) are smoothly dispersed in the material, and examples of the dispersion solution may include an aqueous dispersion solution.

The spraying is preferably an ultrasonic spraying, and the ultrasonic spraying is preferably performed at 1 to 2 MHz.

It is preferable that the fine liquid droplets manufactured using the ultrasonic spraying of the dispersion solution are conveyed to the dry furnace using convey gas including inert gas and dried in the dry furnace, and the temperature of the dry furnace is 150 to 250° C.

The precursor powder obtained using the ultrasonic spraying and the drying of the dispersion solution is reduced by heat treatment, and the reduction heat treatment is preferably performed in an inert gas atmosphere at the temperature of 700 to 900° C. for 20 to 60 min.

FIG. 1 shows a result of an x-ray diffraction analysis of manufactured graphene oxide after graphite (alfa Aesar, natural, −200 mesh, #40795) is oxidized using a Modified Hummers process as a liquid phase chemical reaction to manufacture graphene oxide. The Modified Hummers method is described in detail in the document by Cote, et. al., (Cote, L. J.; Kim, F.; Huang, J. J. Am. Chem. Soc. 2009, 131, 1043-1049).

Figure 2:
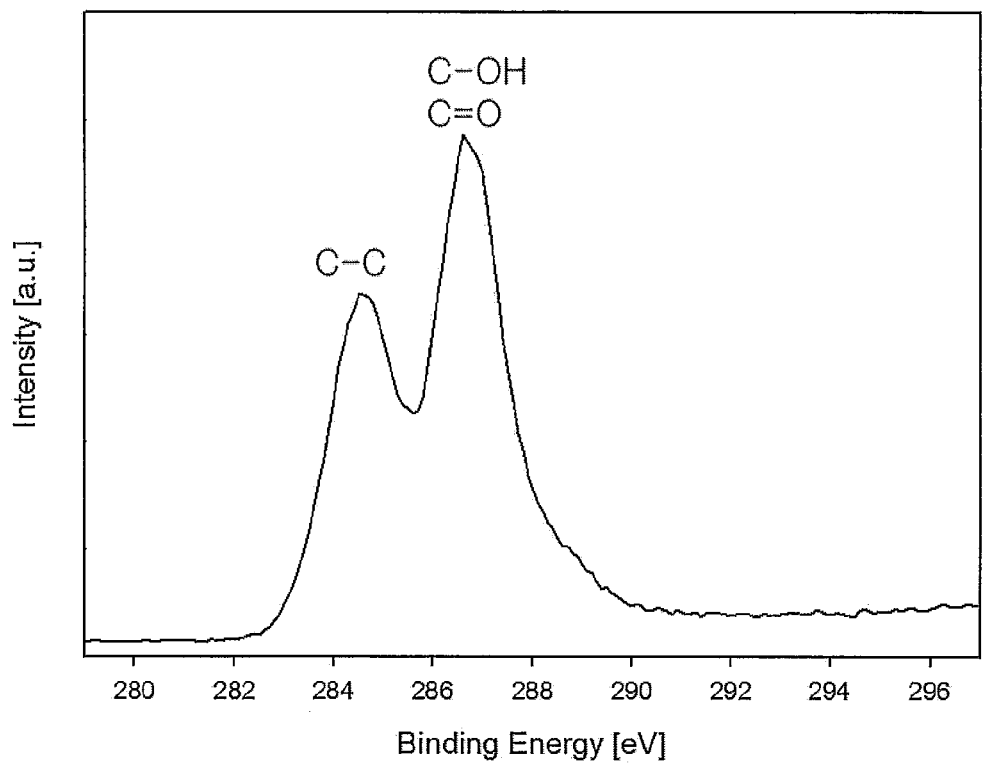
FIG. 2 shows a result of an x-ray photoelectron spectroscopy (XPS) analysis of graphene oxide.
Figure 2:
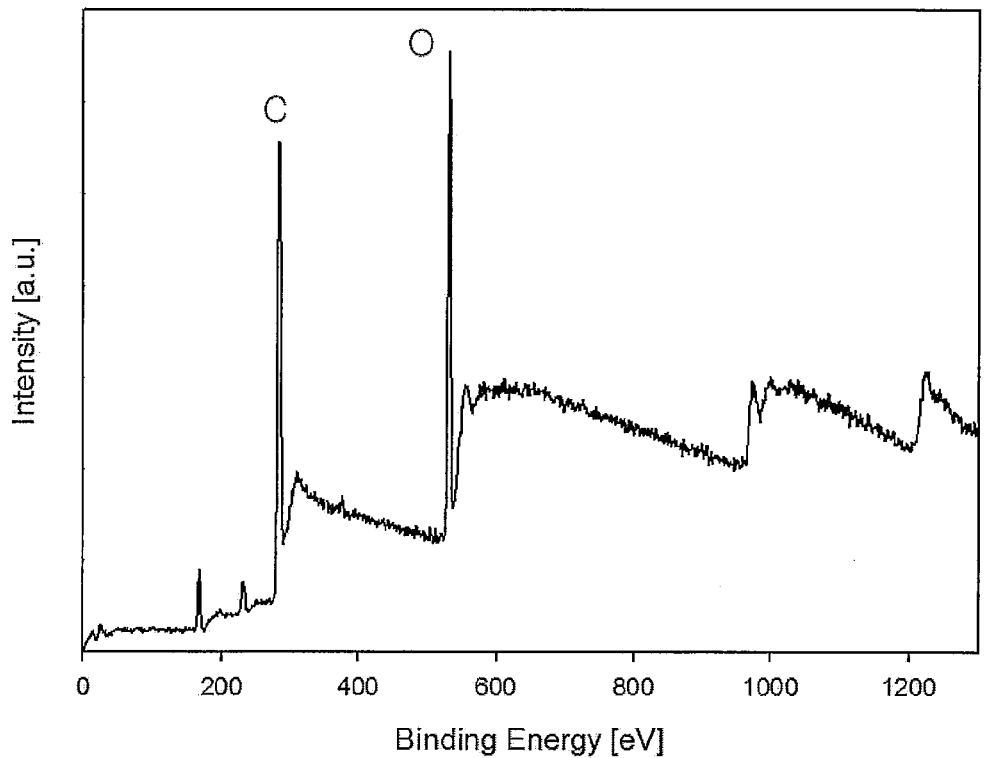
Figure 3:
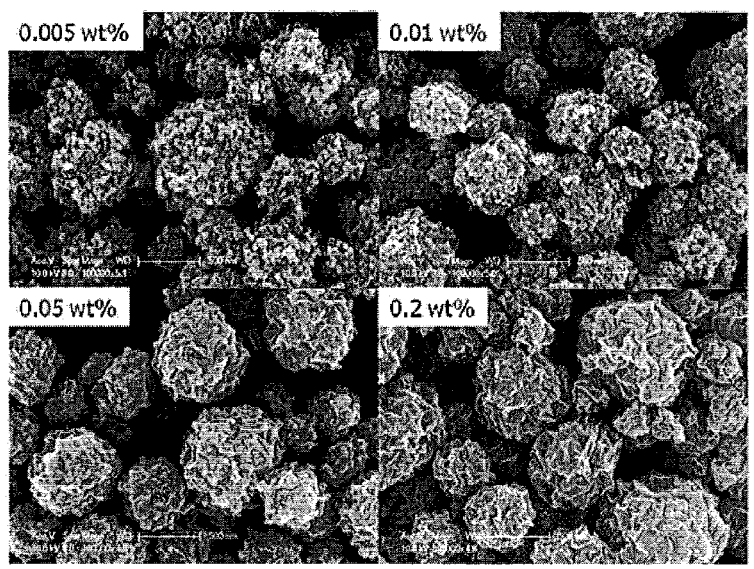
FIG. 3 is a scanning electron microscopic picture showing titanium dioxide-graphene composite powder depending on a content of graphene oxide included in a dispersion solution.

FIG. 2 shows a result of an x-ray photoelectron spectroscopy (XPS) analysis of graphene oxide, and it was confirmed that graphene oxide was manufactured shown in FIGS. 1 and 2. FIG. 3 is a scanning electron microscopic picture showing the composite powder manufactured using a process including spraying the aqueous dispersion solution including 0.1 wt % of titanium dioxide (Degussa, P25) and 0.005, 0.01, 0.05 or 0.2 wt % of manufactured graphene oxide using the ultrasonic sprayer (UN-511, Alfesa Pharm Co. Japan, resonator frequency: 1.7 MHz), conveying the sprayed fine liquid drops using Ar (flow rate: 1 L/min) to the dry furnace preheated at 200° C. to form the dried precursor powder, containing the manufactured precursor powder in the alumina boat, and heat treating the powder in an Ar atmosphere (flow rate: 1 L/min) at 800° C. for 30 min.

The term "wt. %" described in the upper part of the left of each scanning electron microscopic picture of FIG. 3 means wt. % of graphene oxide included in the aqueous dispersion solution.

From FIG. 3, it can be seen that when the content of graphene oxide is as high as 0.05 to 0.2 wt. %, the structure includes the $TiO_2$ porous body totally covered with graphene at the surface thereof, and when the content of graphene oxide is as low as 0.005 to 0.01 wt %, the $TiO_2$ porous body is shown and graphene is loosely connected.

Figure 4:
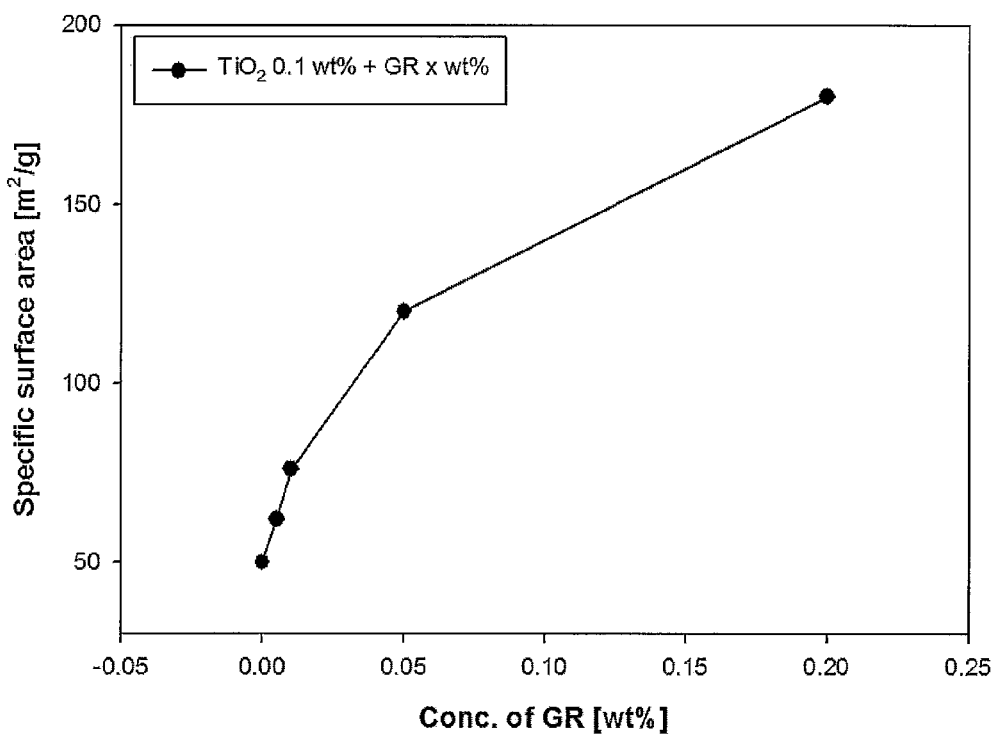
FIG. 4 shows a result of measurement of a specific surface area (BET) of titanium dioxide-graphene composite powder depending on a content of graphene oxide included in the dispersion solution.

FIG. 4 shows a result of measurement of a specific surface area (BET) of manufactured titanium dioxide-graphene composite powder. When graphene is not mixed, the specific surface area is 50 $m^2/g$, and when graphene is mixed in the content of 0.2 wt %, the specific surface area is increased to 180 $m^2/g$, and it can be seen that the surface of $TiO_2$ having the porous structure is covered with graphene having the wide specific surface area to increase the specific surface area.

Figure 5:
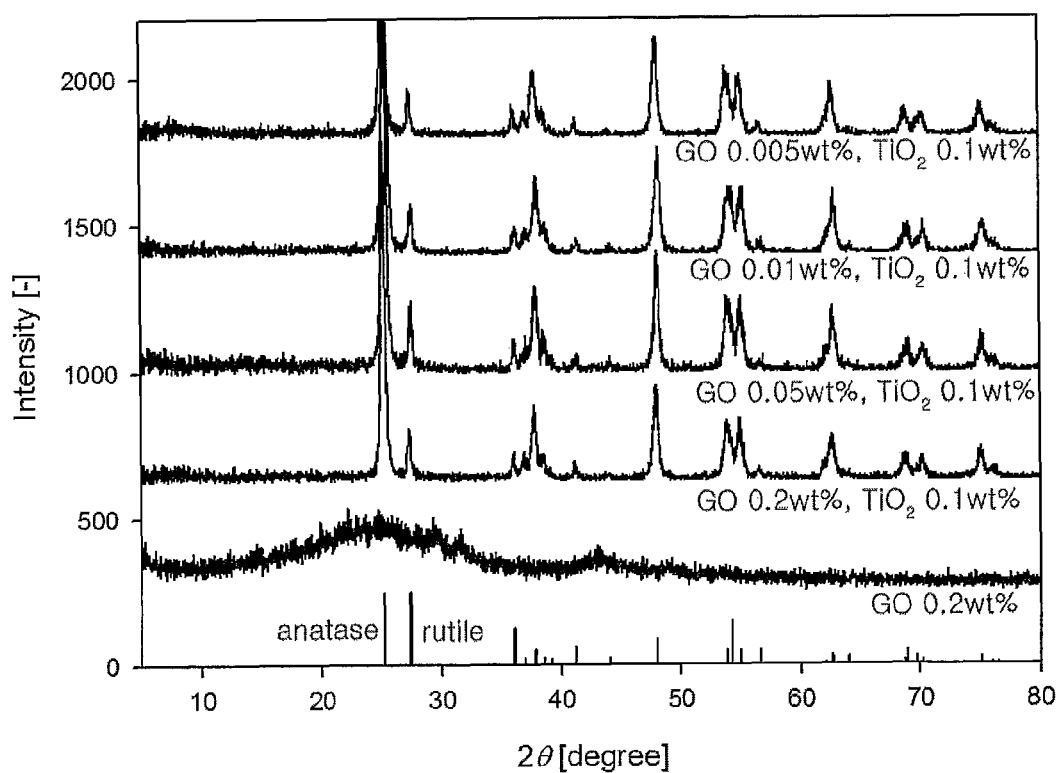
FIG. 5 shows a result of an X-ray diffraction analysis of titanium dioxide-graphene composite powder depending on a content of graphene oxide included in the dispersion solution.
Figure 6:
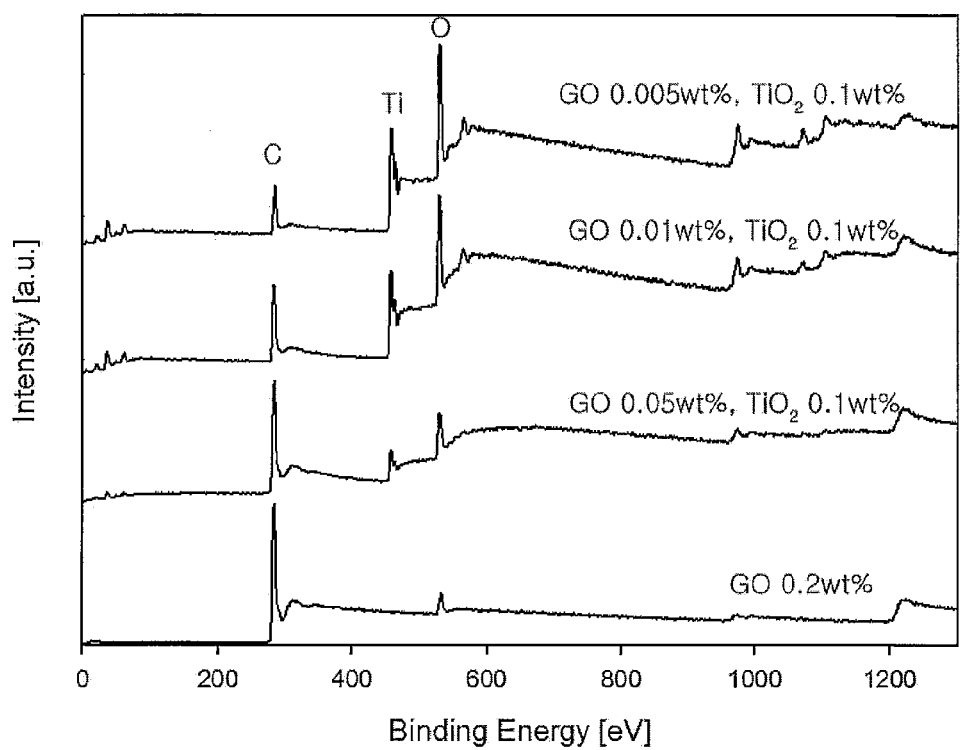
FIG. 6 shows a result of an X-ray photoelectron spectroscopy (XPS) analysis of titanium dioxide-graphene composite powder depending on a content of graphene oxide included in the dispersion solution.

FIG. 5 shows a result of an X-ray diffraction analysis of manufactured titanium dioxide-graphene composite powder, and in FIGS. 5 and 6, the term "GO wt. %" means the content of graphene oxide included in the dispersion solution, and the term "$TiO_2$ wt. %" means the content of titanium dioxide included in the dispersion solution. GO of 0.2 wt. % as a comparative example means a result of the powder that is similar to the titanium dioxide-graphene composite of FIG. 4 and manufactured using the dispersion solution not including titanium dioxide-graphene composite but 0.2 wt. % of graphene oxide dispersed therein. From FIG. 5, it can be seen that crystallinities of anatase and rutile of $TiO_2$ are shown in a result of a phase analysis using the X-ray diffractometer.

FIG. 6 shows a result of an X-ray photoelectron spectroscopy (XPS) analysis of manufactured titanium dioxide-graphene composite powder, and it can be seen that as the content of graphene oxide is reduced, the content of carbon component is reduced but the content of titanium and oxygen components is increased.

Figure 7:
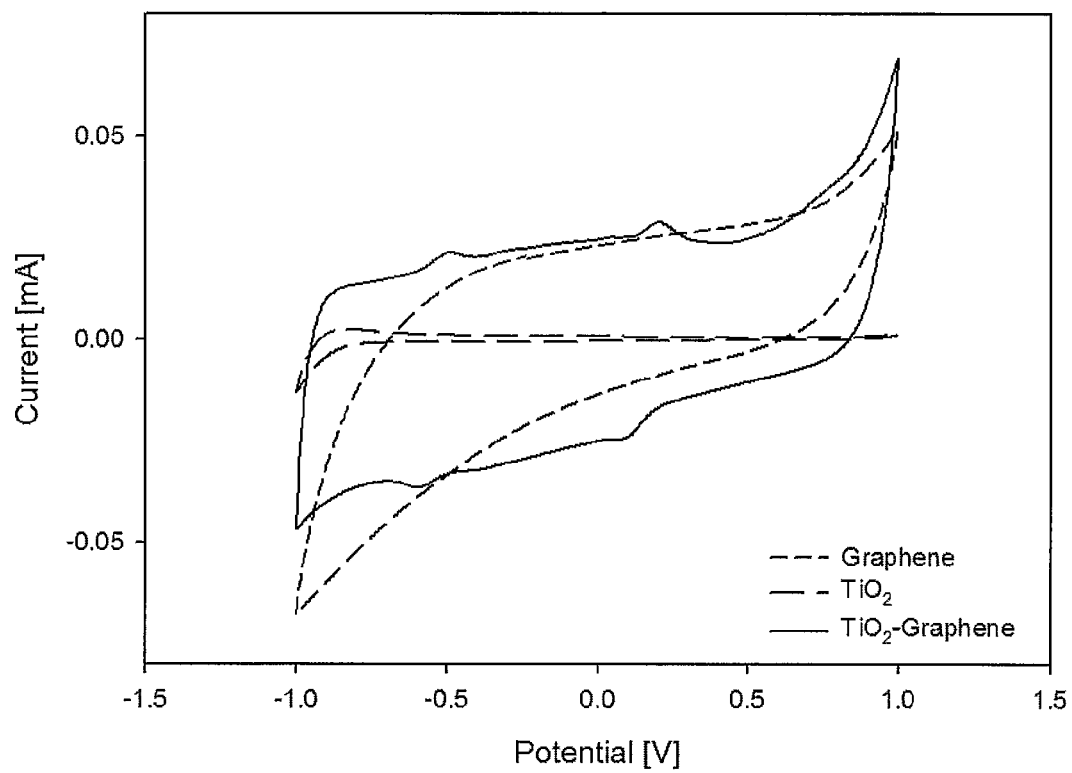
FIG. 7 shows a result of potential-current measurement of a glucose biosensor including a working electrode that includes the titanium dioxide-graphene composite and glucose oxidase.

FIG. 7 shows a result of potential-current measurement of a glucose biosensor including a working electrode including the manufactured titanium dioxide-graphene composite powder and glucose oxidase (Sigma aldrich, Aspergillus niger, 200 units/mg). In detail, 10 mg of the manufactured composite powder was mixed with 10 mg/ml of oxidase (glucose oxidase) to manufacture the solution, and the solution mixture was dropped in the amount of 5 μl on the GCE (glassy carbon electrode) and then dried to manufacture the working electrode, and 2 mM D-(+)-glucose (Sigma aldrich) was used as the reaction solution. The platinum foil and the Ag/AgCl electrode were used as the counter electrode and the reference electrode, and the potentiostat (Bio-logics, Model VSP) was used to evaluate a characteristic of the glucose biosensor. The measurement range was set to −1.0 to 1.0 V, and the measurement rate to 50 mV/sec.

In FIG. 7, titanium dioxide-graphene (graphene-$TiO_2$) means a result of measurement of the sensor including the composite powder manufactured using the dispersion solution including 0.01 wt % of graphene oxide and oxidase provided on the working electrode, and graphene or $TiO_2$ as a comparative example means a result of measurement of the sensor including pure graphene used instead of the composite powder or the mixture of titanium dioxide and oxidase provided on the working electrode.

In FIG. 7, a characteristic of the glucose biosensor is evaluated using a cyclic voltammetry, when degrees of current flow of graphene, titanium dioxide, and the graphene-titanium dioxide composite are compared, in the case of the sensor including the graphene-titanium dioxide composite, the degree of current flow is strongest, and oxidation and reduction are strongly shown at −0.5 V and −0.6 V.

Figure 8:
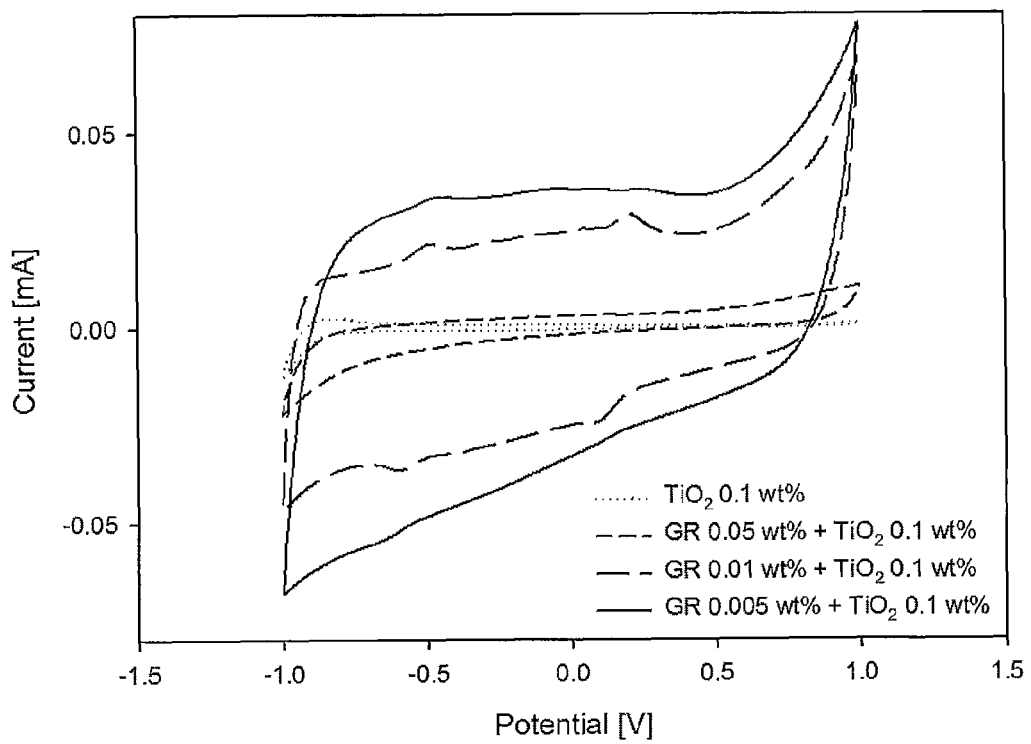
FIG. 8 shows a result of potential-current measurement of the glucose biosensor including the working electrode that includes the titanium dioxide-graphene composite and glucose oxidase depending on the content of graphene oxide included in the dispersion solution.

FIG. 8 shows a result of measurement of a characteristic of the glucose biosensor for each content of graphene oxide of the composite manufactured depending on the content of graphene oxide included in the dispersion solution. In FIG. 8, the term "GR wt. %" means the content of graphene oxide included in the dispersion solution, and the term "$TiO_2$ wt. %" means the content of titanium dioxide included in the dispersion solution. $TiO_2$ of 0.1 wt. % as a comparative example means the case where titanium dioxide powder that is similar to the composite of FIG. 4 and manufactured using the dispersion solution not including titanium dioxide-graphene composite but titanium dioxide dispersed therein is provided on the working electrode.

From FIG. 8, it can be seen that as the content of graphene oxide in the dispersion solution is reduced, the current flow is increased. Accordingly, it can be seen that the composite including the porous titanium dioxide agglomerate partially covered with graphene on the surface thereof has a current flow that is more smooth than that of the composite including the porous titanium dioxide agglomerate totally covered with graphene on the surface thereof and than that of the case where both titanium dioxide and graphene are exposed to the surface of the working electrode to increase sensitivity.

According to the exemplary embodiments of the present invention, a glucose sensor prepared by a composite of graphene oxide and titanium dioxide, which is obtained by spraying a dispersion solution, drying and heat treating, may provide features that allow a current flow to be excellent, a current to sensitively change depending on a change in electric potential, sensitivity to be high, and a low voltage characteristic be excellent.

What is claimed is:
1. A method of making a glucose sensor comprising:
   a titanium dioxide-graphene composite having a porous structure; and
   a dispersion solution comprising graphene oxide and titanium dioxide, the dispersion solution containing 5 to 10 parts by weight of the graphene oxide based on 100 parts by weight of the titanium dioxide is sprayed dropwise, sprayed liquid droplets are dried to obtain precursor powder of graphene oxide-titanium dioxide, and the precursor powder is heat treated to manufacture the composite and a portion of the surface of porous agglomerate of titanium dioxide is covered with graphene to form a secondary particle structure.

2. The method of making a glucose sensor of claim 1, wherein the glucose sensor comprises an electrode to which a glucose oxidase or a glucose dehydrogenase and the composite are fixed.

3. The method of making a glucose sensor of claim 1, wherein the dispersion solution is sprayed using an ultrasonic wave and the sprayed liquid droplets are conveyed to a dry furnace by an inert gas to manufacture the precursor powder.

4. The method of making a glucose sensor of claim 1, wherein the precursor powder of the graphene oxide-titanium dioxide is heat treated in an inert gas atmosphere at 700 to 900° C. to manufacture the composite.

5. The method of making a glucose sensor of claim 1, wherein the composite has a specific surface area of 55 to 200 $m^2/g$.

* * * * *

UNITED STATES PATENT AND TRADEMARK OFFICE
CERTIFICATE OF CORRECTION

| | | |
|---|---|---|
| PATENT NO. | : 8,562,815 B2 | Page 1 of 1 |
| APPLICATION NO. | : 13/283018 | |
| DATED | : October 22, 2013 | |
| INVENTOR(S) | : Hee Dong Jang et al. | |

It is certified that error appears in the above-identified patent and that said Letters Patent is hereby corrected as shown below:

Title Page, Item (56), References Cited, Other Publications, Column 2, Line 2, delete "Gluose" and insert -- Glucose --

In the Claims

Column 7, Line 1, Claim 2, delete "making a" and insert -- making the --

Column 7, Line 5, Claim 3, delete "making a" and insert -- making the --

Column 7, Line 9, Claim 4, delete "making a" and insert -- making the --

Column 7, Line 13, Claim 5, delete "making a" and insert -- making the --

Signed and Sealed this
Eleventh Day of March, 2014

Michelle K. Lee
*Deputy Director of the United States Patent and Trademark Office*